(12) United States Patent
Bauer et al.

(10) Patent No.: US 7,996,172 B2
(45) Date of Patent: Aug. 9, 2011

(54) SYSTEM AND A METHOD FOR MANAGING SAMPLE TEST RESULTS AND RESPECTIVE SAMPLE RESULT CONTEXT INFORMATION

(75) Inventors: Ralf Bauer, Frankenthal (DE); Louis-Pierre Gagnaux, Mettmenstetten (CH); Luis Suarez Novau, Barcelona (ES)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 324 days.

(21) Appl. No.: 12/277,989

(22) Filed: Nov. 25, 2008

(65) Prior Publication Data

US 2009/0177427 A1 Jul. 9, 2009

Related U.S. Application Data

(63) Continuation of application No. PCT/EP2007/004582, filed on May 23, 2007.

(30) Foreign Application Priority Data

Jun. 1, 2006 (EP) .................................... 06011417

(51) Int. Cl.
*G06F 11/00* (2006.01)

(52) U.S. Cl. .................................................. 702/85
(58) Field of Classification Search .................. 702/23, 702/85, 182–185, 188
See application file for complete search history.

(56) References Cited

U.S. PATENT DOCUMENTS

| 5,841,975 | A | 11/1998 | Layne et al. |
| 6,581,012 | B1 | 6/2003 | Aryev et al. |
| 6,721,615 | B2 | 4/2004 | Fava et al. |
| 2004/0033501 | A1 | 2/2004 | Lappe et al. |
| 2008/0091471 | A1* | 4/2008 | Michon et al. ............... 705/3 |

FOREIGN PATENT DOCUMENTS

| EP | 1376444 A1 | 6/2002 |
| EP | 1 248 170 A1 | 10/2002 |
| WO | 98/26365 | 6/1998 |
| WO | 0193762 A2 | 12/2001 |
| WO | 03065033 A2 | 8/2003 |
| WO | 2007/137750 A1 | 12/2007 |

* cited by examiner

*Primary Examiner* — Edward Raymond
(74) *Attorney, Agent, or Firm* — Dinsmore & Shohl LLP

(57) ABSTRACT

A system and method for managing sample test results and respective sample result context information within a laboratory environment are disclosed. The system provides an analytical unit configured to run at least one test on a sample, and a management unit connected with the analytical unit for data interchange, wherein said management unit is configured to save and display on demand sample test results and respective sample result context information, to control dynamically at least one actual value of at least one item of the respective sample result context information with respect to a scheduled threshold value and to initiate at least one action when the actual value corresponds to the scheduled threshold value according to a predefined execution plan schedule. Furthermore, embodiments referring to an appropriate management unit and a method for managing sample test results and respective sample result context information within a laboratory environment are also disclosed.

41 Claims, 6 Drawing Sheets

| Workarea | Quality Control | Validation | Master Files | Parameters |
|---|---|---|---|---|

| Validation | Manual Results | Result Context |
|---|---|---|

Sample ID: [ ]
Patient ID: 23436454
Date of Birth: 17.06.1961
Order Date/Time: 29.09.2004

Name: Miller
Name: Ralf
Sex: Male
Req/Ward: MK2

◆ 24h  ◇ All  ◇ [ ] Days

| Sample Priority | Sample-ID | Sample result date and time | | | Sample Comment |
|---|---|---|---|---|---|
| | ☐ 1111 | 11.08.2004 17:35:02 | | | |
| | 4444 | 02.05.2004 17:32:45 | | | |
| | 4546 | 14.04.2004 17:25:12 | | | |
| ✚ | 4548 | 14.04.2004 09:10:43 | | | |
| ✚ | 232323 | 02.09.2004 12:08:43 | | | |
| ✚ | ◯ 2435213 | 02.05.2002 13:34:51 | | | |
| | 2438353 | 02.07.2004 15:02:08 | | | |

[Details]

FIG. 4A

| Workarea | Quality Control | Validation | Master Files | Parameters | | | |

Toolbar: Status, Utilities, Alarms, Help, Print, Labels, Exit

Validation | Manual Results | Result Context

Sample ID: [ ]  Patient ID: 234364454  Date of Birth: 17.06.1961  Order Date/Time: 29.09.2004
Name: Miller  Surname: Ralf  Sex: Male  Req/Ward: MK2

◆ 24h  ◇ All  ◇ ☐ Days

| Test | Result | Result date and time | Validator | Reagent Lot | Control Code | Control Result | Control Lot | Calibrator Name | Calibrator Lot |
|---|---|---|---|---|---|---|---|---|---|
| Na | 147 | 11.08.2004 17:35:02 | System | 234234554 | PPU | 110,5 | 345826782 | Calib-A | 6786069 |
|  |  |  |  |  | PNU | 143,6 | 65790877 |  |  |
| Alb | 38 | 11.08.2004 17:35:02 | System | 234234554 | PPU | 13,2 | 345826782 | Calib-A | 6786069 |
|  |  |  |  |  | PNU | 16,3 | 65790877 |  |  |
| Crea | 68 | 11.08.2004 17:35:02 | Igor | 54754867 | Lypocheck A | 143,2 | 327452354 | Calib-A | 6786069 |
|  |  |  |  |  | Lypocheck B | 367,4 | 65754775 |  |  |
|  |  |  |  |  | Lypocheck C | 235,4 | 70809488 |  |  |
| GGT | 68 | 11.08.2004 17:35:02 | Manager | 6798788686 | GGT_P | 186 | 134437667 | Calib-GGT | 907868232 |
| 405 | 406 | 407 | 408 | 409 | 410 | 411 | 412 | 413 | 414 |

Sample Record  Close  Print

Details

SYSTEM AND A METHOD FOR MANAGING SAMPLE TEST RESULTS AND RESPECTIVE SAMPLE RESULT CONTEXT INFORMATION

CROSS REFERENCE TO RELATED APPLICATIONS

This application is a continuation of International Application No. PCT/EP2007/004582 filed 23 May 2007, which claims priority to EP Application No. 06011417.0, filed Jun. 1, 2006, which are herein incorporated by reference.

FIELD OF THE INVENTION

The present disclosure relates to a system and a method for managing sample test results and respective sample result context information within a laboratory environment. Furthermore, the present disclosure relates to a management unit for managing sample test results and respective sample result context information. The present disclosure also refers to an appropriate computer program, a computer program product and a computer-readable medium.

BACKGROUND OF THE INVENTION

Clinical laboratories are producing hundreds to thousands of patient sample test results per day. In case of reported test results outside a normal range or other irregularities, e.g. delta check violation, a requester maybe is starting appropriate actions, as for example a medical therapy. As this is a very sensitive area, laboratories have to store patient sample test results for a long time period in case of potential injuries or a brought in accusation. Such a time period can be up to 15 years.

Therefore, the corresponding laboratory is obliged to save besides the pure patient sample test result also the respective sample result context information to verify on demand how and under which conditions a certain patient sample test result has been generated, for example by a certain analytical unit. This complete information, i.e. the patient sample test result and the corresponding sample result context information, has to be recorded in order to show on demand that the corresponding laboratory is operating according to national regulations, international standards or internal quality SOP's.

Each reagent package which is used for a specific patient sample test is associated with a reagent lot number. Similarly, a control material used for a quality control measurement to check if a specific analytical unit is under control is associated with a quality control lot number. A calibrator material which is used for calibration purposes is also associated with a calibrator lot number.

In addition, a laboratory always has to provide a predefined reservoir of the different mentioned materials, namely of reagent packages, of quality control material and of calibrator material so that the laboratory is always capable to perform a specific test on a patient sample on demand. Within a laboratory environment it is very important in favor of security that those materials are always available in a sufficient predefined quantity.

The different lot numbers are included within the above mentioned sample result context information and is therefore directly associated with a corresponding sample test result.

Currently, the sample test results and the respective sample result context information is stored in different sources, as for example in a host system, an analytical unit or a paper printout. Furthermore, the reservoir of the different materials which has to be available on demand in case that a certain sample test has to be performed, is currently controlled separately.

SUMMARY OF THE INVENTION

Therefore, it would be desirable to provide a method and a system for managing sample test results and respective sample result context information within a laboratory environment at one place in an easy and convenient way.

According to one embodiment, a system for managing sample test results and respective sample result context information within a laboratory environment is provided, wherein the system comprises at least one analytical unit configured to run at least one test on a sample, and a management unit connected with the at least one analytical unit for data interchange. The management unit is configured to save and display on demand sample test results and respective sample result context information, to control dynamically at least one actual fulfilment level of at least one item of the respective sample result context information with respect to a scheduled fulfilment level and to initiate at least one action as soon as the actual fulfilment level corresponds to the scheduled fulfilment level according to a predefined execution plan schedule.

In another embodiment, a management unit for managing sample test results and respective sample result context information within a laboratory environment is disclosed. The management unit comprises a database to save the sample test results and the respective sample result context information, output means able to display on demand the sample test results and the respective sample result context information, connecting means able to download the sample test results and the respective sample result context information from at least one analytical unit and means able to control dynamically at least one actual fulfilment level of at least one item of the respective sample result context information with respect to a scheduled fulfilment level and to initiate at least one action as soon as the actual fulfilment level corresponds to the scheduled fulfilment level according to a predefined execution plan schedule.

Furthermore, in yet another embodiment, a method for managing sample test results and respective sample result context information within a laboratory environment is disclosed. The method comprises running at least one test on at least one sample by means of at least one analytical unit, transferring the corresponding sample test results and the respective sample result context information from the at least one analytical unit to a management unit connected with the at least one analytical unit for data interchange, storing the sample test results and the respective sample result context information, displaying on demand the sample test results and the respective sample result context information, controlling at least one actual value of at least one item of the respective sample result context information with respect to a scheduled threshold value, and initiating at least one action in case that the actual value corresponds to the scheduled threshold value according to a predefined execution plan schedule.

Further features and embodiments will become apparent from the description and the accompanying drawings.

BRIEF DESCRIPTION OF THE DRAWINGS

FIG. 4 shows an abridgement of a dialog conductible by means of a system according to the present disclosure.

FIG. 5 shows a screenshot as it can be displayed for a user according to a possible implementation of the disclosure.

DETAILED DISCUSSION

Figure 1:
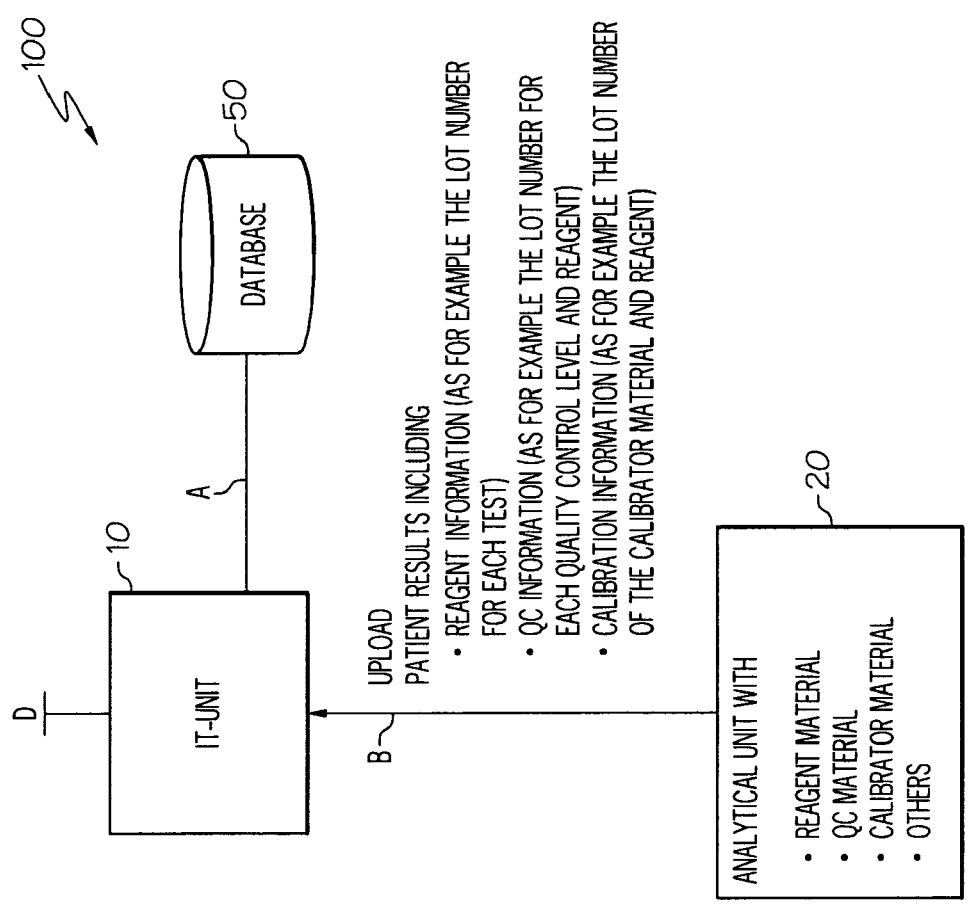
FIG. 1 shows a schematic block diagram of a possible embodiment of a system according to the present disclosure.

For purposes of clarity, the present discussion refers to an abstract example of a system. However, the method and the system may operate with a wide variety of types of network systems including networks and communication system dramatically different from the specific example as illustrated in the following drawings.

It should be understood that while the implementation is described in terms of a specific system, that there are applications in a variety of communication systems, such as advanced medical laboratory systems, advanced laboratory networks or any other communication systems that would benefit from the system or the method according to the present disclosure. It is intended that the system used in the specification and claims is suitable to be used in any communication system unless the context requires otherwise.

A possible implementation is schematically illustrated in the drawings by way of an example embodiment and is explained in detail with reference to the drawings. It is understood that the description is in no way limiting on the scope of the present disclosure and is merely an illustration of various implementations.

In the following, similar components are referred to by equal reference numbers.

FIG. 1 shows a block diagram of an embodiment of the system according the present disclosure. The system 100 comprises a management unit 10, at least one analytical unit 20 and a database 50. It is possible that a plurality of analytical units 20 are provided which all are connectable to the management unit 10. Furthermore, the system 100 can also comprise at least one pre-analytical unit and/or at least one post-analytical unit, which are not shown here.

The management unit 10 is connected with the database 50 as indicated by a link A. The database 50 can also be integrated within the management unit 10. The management unit 10 can be connected, as indicated by line D, with a host component (not shown here). Via standard host interface protocols, e.g. ASTM or HL7, the management unit 10 can communicate with such a host component with a standard function set. No specific logic has to be realized in the host system. Therefore, it can be integrated fast, easy and with low risk.

The analytical unit 20 is able to perform one or more specific tests on a sample. Such a specific test requires a certain reagent material which is generally provided in form of a reagent package. Before a test is done on a sample, a quality control measurement is performed by means of a specific quality control material in order to check if the analytical unit 20 is under control. Furthermore, a specific calibrator material is used for calibration purposes of the analytical unit.

When a test is performed on a sample of a patient, the analytical unit 20 is uploading the received sample test result to the management unit 10. It is possible that such sample test result is transferred automatically or semi-automatically into the management unit 10. The analytical unit 20 is uploading the sample test result together with respective sample result context information. Such an upload can generally be done via a communication interface. The uploaded result context information includes several items assigned or associated to the corresponding test result. A reagent lot number of the reagent package which has been used for the sample test is uploaded to the management unit 10. The reagent lot number is uploaded from the analytical unit 20 to the management unit 10 with each patient sample result. A quality control lot number of the quality control material used for the quality control measurement to check if the analytical unit 20 is under control is also uploaded from the analytical unit 20 to the management unit 10, when the quality control result is uploaded. A calibrator lot number of the calibrator material used for calibration purposes is also uploaded from the analytical unit 20 to the management unit 10 as soon as the corresponding calibration process has been finished. Optionally, a calibrator result can also be transferred into the management unit 10.

Depending on the throughput of the communication line of the analytical unit, the analytical unit is transferring with each single patient test result the reagent lot number of the reagent used for the measurement, the quality control lot number of all quality control levels valid at measurement time for this reagent/test, and the calibrator lot number used for this reagent/test, optionally including the calibrator values and calibrator curves.

The management unit 10 transfers the received information together with the corresponding sample test result to the database 50, where the patient sample result as well as its result context information can be stored and retrieved on demand. It is possible that the management unit 10 provides a graphical user interface via which a user can access the management unit in order, for example, to retrieve and to check a specific patient sample result as well as the corresponding result context information. Via such a user interface it is possible to display the complete set of information at one place in an easy and convenient way.

Besides the possibility of the system to store and display on demand patient sample test results as well as the respective result context information of one or more samples of the patient, the management unit 10 can also use the result context information to control dynamically at least one actual value of at least one item of the respective sample result context information with respect to a scheduled threshold value. It is possible for example, that a scheduled stock of reagent packages is stored within the management unit 10 and is dynamically compared with the actual reagent consumption. As soon as the actual stock falls below a predefined value given for example by the scheduled stock, the management unit 10 initiates at least one action according to a predefined execution plan schedule. Such an action can be for example the output of a signal to a user indicating to the user that the actual stock of the reagent material has reached a minimum level. Alternatively, the management unit 10 can also trigger as soon as the actual stock of the reagent material undergoes the predefined value re-ordering of the reagent material. This can be done automatically. The signal can be realized in different ways. This can be an acoustic signal, a visual signal or a printout listing the actual stock of the reagent material. There are a lot of further possible examples how such a signal can be realized.

As described with respect to the reagent material, the same dynamical control can be performed by the management unit 10 with respect to the quality control material and the calibrator material.

An action which can be initiated as soon as an actual value corresponds to a scheduled threshold value can also be an evaluation in order to optimize several process sequences. It is possible for example to evaluate an actual consumption.

Figure 2:
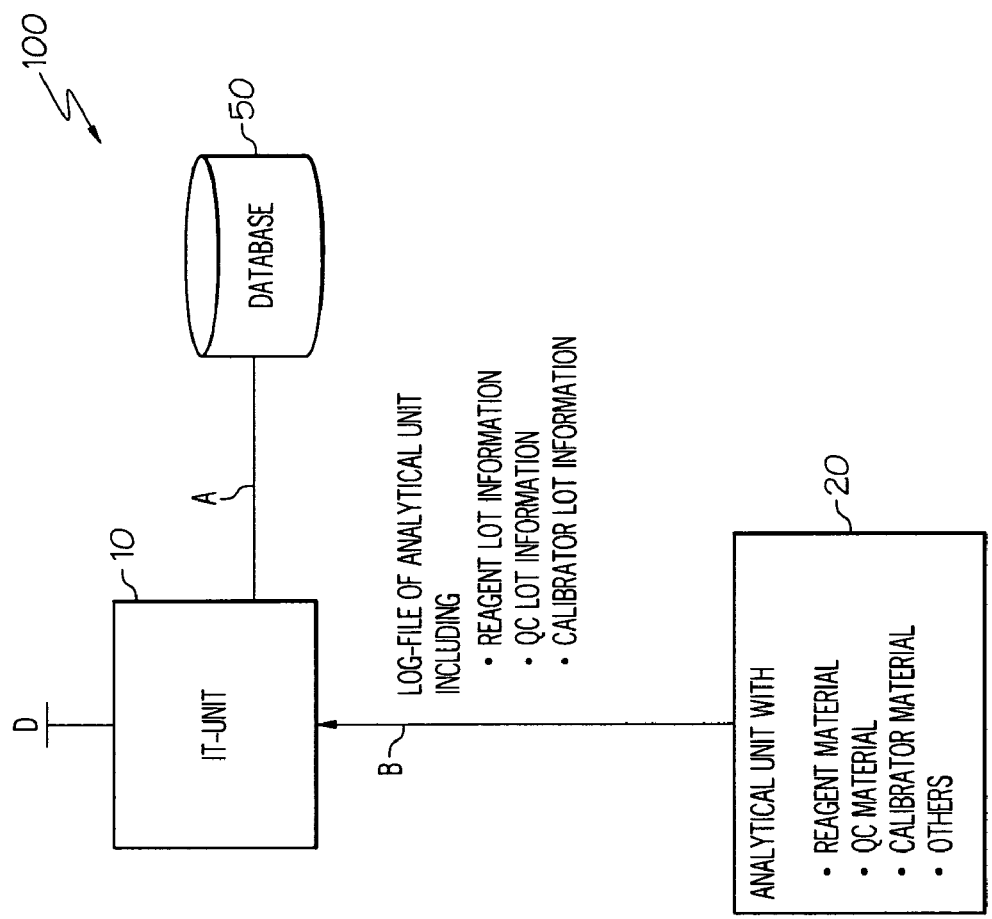
FIG. 2 shows a schematic block diagram of a further possible embodiment of a system according to the present disclosure.

FIG. 2 shows a block diagram of a further embodiment of a system according to the present disclosure. The system 100 comprises a management unit 10, at least one analytical unit 20 and a database 50. The database 50 is connected as indicated by link A to the management unit 10. Alternatively, the database 50 can also be an integral part of the management unit 10. The management unit 10 is again connectable via a standard communication interface to a host component which is not shown here. The analytical unit 20 is in contact for data interchange with the management unit 10 as indicated by arrow B. In the example shown in FIG. 2 the analytical unit 20 is uploading a log-file periodically to the management unit 10. Part of the log-file information is a quality control log number of a quality control material used for a quality control measurement to check if the analytical unit 20 is under control. The log-file information also includes a calibrator information as a calibrator result and a calibrator lot number of a calibrator material used for calibration purposes. Due to the size of the log-file the log-file can be transferred via a high-speed network connection to the management unit 10. The management unit 10 is afterwards filtering the appropriate information out of the log-file for a consolidated data view. The log-file as proposed here is a file that lists and records actions that have occurred. The analytical unit 20 can maintain a log-file listing every lot number associated with the performance of a certain actual sample test. Besides the lot number information of the reagent, quality control and calibrator data among other information, the following other data are provided in the log-file:

Number of determinations per bottle, currently available and total. This information can be used to compare the current consumption with the material available on the analytical unit and can be combined with the stock information for ordering purposes;

Expiration date for quality purposes: "can the material still be used for patient result measurement?" In case of conflicts an alarm can be generated in the management unit;

Operator ID's for quality and tracking reasons: "who has done which action and at which time in the process on the analytical unit?";

Target values for quality purposes: warning information in case of differences to current defined values on the management unit.

Figure 3:
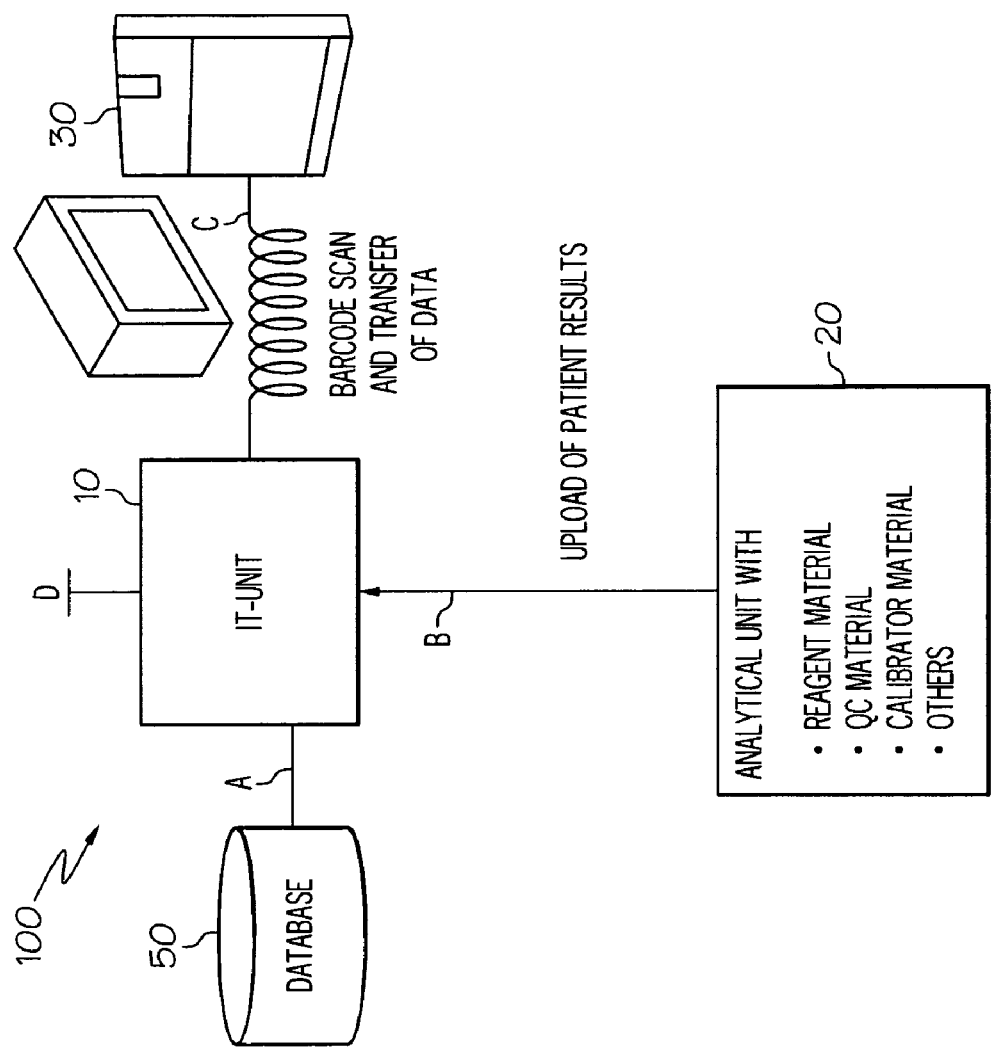
FIG. 3 shows a schematic block diagram of another possible embodiment of a system according to the present disclosure.

FIG. 3 shows a further embodiment of a system according to the present disclosure. The system 100 comprises here a management unit 10 and a database 50 which is connected via link A to the management unit 10. An analytical unit 20 is in connection with the management unit 10 via link B. The management unit 10 is further connected with a barcode scanner 30. Via the connection C it is possible to transfer data from the barcode scanner 30 to the management unit 10 and via link A to the database 50.

In the example shown in FIG. 3, a label with a two dimensional barcode is available on each reagent package, each quality control package and each calibrator package. Those two dimensional barcodes have besides other information quality control information and calibrator information which is required to give a complete information about a certain sample test result and is part of the sample result context information. Those barcode information can be scanned into the database 50 of the management unit 10. This scan can be performed by the barcode scanner 30 and the scanned barcode information can afterwards be transferred to the management unit 10 and saved in the database 50. With each patient test result received from the analytical unit 20 the appropriate quality control information and calibrator information is linked. As already described with respect to FIGS. 1 and 2 the material scanned is used for stock management. This information about the actual stock of the different materials as for example the reagent material, the quality control material and the calibrator material enables the management unit 10 to control dynamically the actual stock of the different materials and to initiate, if necessary, a pre-defined action as soon as the actual stock of the different materials reaches a minimum value so that a re-ordering of the respective material can be triggered. As already mentioned above the action can be realized in form of a warning signal, as for example an acoustic or a visual signal or it can be realized by an automatic re-ordering of the material in question.

FIG. 4 shows a sequence of two possible screenshots as they can be provided on an appropriate result context screen which is part of an embodiment of a system according to the present disclosure. The result context screen is intended to show on demand information of one or more samples belonging to a specific patient. The complete information includes a sample test result and the respective sample result context information. The following is just describing proposals how such a function can be realized.

To retrieve the samples belonging to a specific patient and to display the sample information including the sample result context information, a dialog via a graphical user interface is started to filter and search in a database connected to a management unit for the appropriate patient and the assigned sample(s). Different search criteria can be supported. Useful search criteria to find the requested patient including sample information in the database of the management unit are a patient-ID, a patient name, a patient date of birth, a sample order date/time, a sample-ID and a time/date selection. Those search criteria can be feed into the management unit via respective assigned entry fields of the dialog as indicated in area A of FIG. 4a. Those entry fields are exemplary for useful search criteria to find a requested patient including sample information in the corresponding database. It is useful to support wildcards in several entry fields as for example in the patient name, the patient-ID and the sample-ID entry field.

After a selection has been done a query is started. As a result of the performed query all samples belonging to a specific patient are listed fulfilling the inputted search criteria. Such a list is exemplarily shown in area B of FIG. 4a. The table 400 shown in FIG. 4a is divided into four different columns 401, 402, 403 and 404. Column 401 discloses a sample priority, column 402 identifies a sample-ID, column 403 gives information about an assigned sample result and date and time about that sample result, column 404 shows sample comments. The window 40 shown in FIG. 4a can be displayed on an appropriate result context screen.

Besides the different entry fields, there are different specified buttons which can be pressed in order to open new functional windows. When the details button C is pressed, the sample information of the selected line, as indicated by a black background, is displayed. In the example shown in FIG. 4a this is a sample with a sample-ID 1111. The dialog is shown in FIG. 4b. The dialog shows the patient sample including patient sample result context information. Column 405 is titled as "Test". This column displays the tests requested in the patient sample. The next column 406 called "Result" shows the respective results of the requested tests. Test results released outside a normal range are indicated by a yellow or red background color depending on the configured warning level. Column 407 "Result date and time" displays the measurement date and time of the test. Depending of the capabilities of the analytical unit, the measurement date and time of the analytical unit or the received date and time for the result in the management unit is displayed in this column. Column 408 "Validator" displays a log-in name as configured in the management unit of the validator(s) having done a specific validation, as for example a technical validation and/or a medical/clinical validation of the result. The next column 409 "Reagent Lot" shows the reagent lot number active at the time of the patient result measurement on the analytical unit. A further column not shown here called "Reagent lot expiration time" can be provided in order to show the expiration time of the reagent lot active at the time of the patient result measurement on the analytical unit. Furthermore, there can be provided a further column "Instrument" showing the instrument by means of which the test has been performed.

For all quality control levels the following information is shown in separate columns. Column 410 "Control Code" shows the name of the active control at the time when the patient result has been measured on the instrument. Column 411 "Control Result" shows the released control result at the time of patient result measurement. There can be provided a column "Control measurement date and time" displaying the measurement date and time of the test within the control material. Depending of the capabilities of the analytical unit either the measurement date and time of the analytical unit or the received date and time of the quality control result in the management unit is displayed. A further column can be provided for a "Control validator" showing the name of the validator having released the quality control result. Column 412 "Control Lot" shows the control lot number active at the time of patient result measurement on the instrument. A further column with respect to the quality control levels can be provided, namely a column for the "Control expiration time", showing the expiration time of the control active at the time of patient result measurement on the instrument. A "Control target value" can also be shown in a further column, not shown here, indicating a target value for the test within the quality control material active at the time of patient result measurement on the instrument. A further column named "Control violation flags" can be provided showing the violation flags possibly assigned to the test result within the control material at the time of the patient result measurement on the instrument. It is also possible to foresee a column called "Test comment" showing the comment written either automatically or manually for the test result at the time of the patient test result has been measured on the instrument.

The screenshot shown in FIG. 4b further shows several columns with respect to the calibrator purposes. Column 413 "Calibrator name" shows a calibrator name of the test calibrator used at the time the patient result measurement has been done on the instrument. A further column called "Calibrator Lot" shows the calibrator lot for the test active at the time the patient result measurement has been done on the instrument. There can be provided further columns as for example a column called "Calibrator result" which shows the calibrator test result of the last calibration for this test on the analytical unit. A column called "Calibrator curve" can be shown in a further column for the test valid at the time the patient result measurement has been done on the instrument if those data are provided by the instrument. In a further column the expiration time of the calibrator material can be shown. It has to be noted, that the columns displayed in the screenshot shown in FIG. 4b and the column sequence on the first level is configurable according to the needs of the laboratory.

In a possible implementation, the result context information for reagent material, quality control material and calibrator material is realized for Integra 400/800 systems and the PSM (Process Systems Manager) management software from Roche Diagnostics. Both analytical units are uploading lot information for calibrators, quality control material and reagents currently active and in use for patient result measurement.

The sample result context information is uploaded by extensions implemented in the Integra 400/800 host interface. New queries are implemented allowing the PSM software to get this information. Special error handling is implemented, including the following cases:

Lot number for the material not found:
If no lot number has been found or defined Integra 400/800 systems send a special string ("???????").

Expiration time of the material not available:
If no expiration time has been added to the lot information, the string "00/00/0000" is used and uploaded.

If the Lot Lot-Information is less than 10 characters, spaces on the right hand side will be added. Example: Lot information "N123A" is extended as follows: "N123A [space][space][space][space]".

The following extensions have been implemented in the host interface communication protocol:

For Calibration Data:

| 55 | Test ID | |
|---|---|---|
| 01 | Result Time | |
| 03 | Standard Rates | 1 to y + 1 |
| 04 | Calibration Curve | |
| 05 | Calibrator Lot Information | 1 to 3 |
| 09 | Reagent Lot Information | |
| 00 | Result Data | 1 to m |
| 07 | ABS Sample Check | 0 to y | the calibration curve information is uploaded from the instrument to PSM in field 04, the calibrator lot information is sent in field 05, for specific reagents the field can contain up to 3 lot numbers, the lot number of the calibrated reagent is sent in field 09.

For Quality Control Data:

| 55 | Test ID | |
|---|---|---|
| 01 | Result Time | |
| 09 | Reagent Lot Information | |
| 02 | Control ID | 1 to n |
| 06 | Control Lot Information | |
| 00 | Result Data | | the reagent lot information is uploaded from the instrument to PSM in field 09, the control lot information is sent in field 06.

Depending of the test and control type up to 6 lot numbers are uploaded.

For Patient Samples and Assigned Test Results:

| 53 | Oder ID |
|---|---|
| 55 | Test ID |
| 09 | Reagent Lot Information |
| 00 | Result Data |

For each test result of a patient sample the following information is uploaded:
the reagent lot information for each test result is uploaded from the instrument to PSM in field 09.

Figure 5:
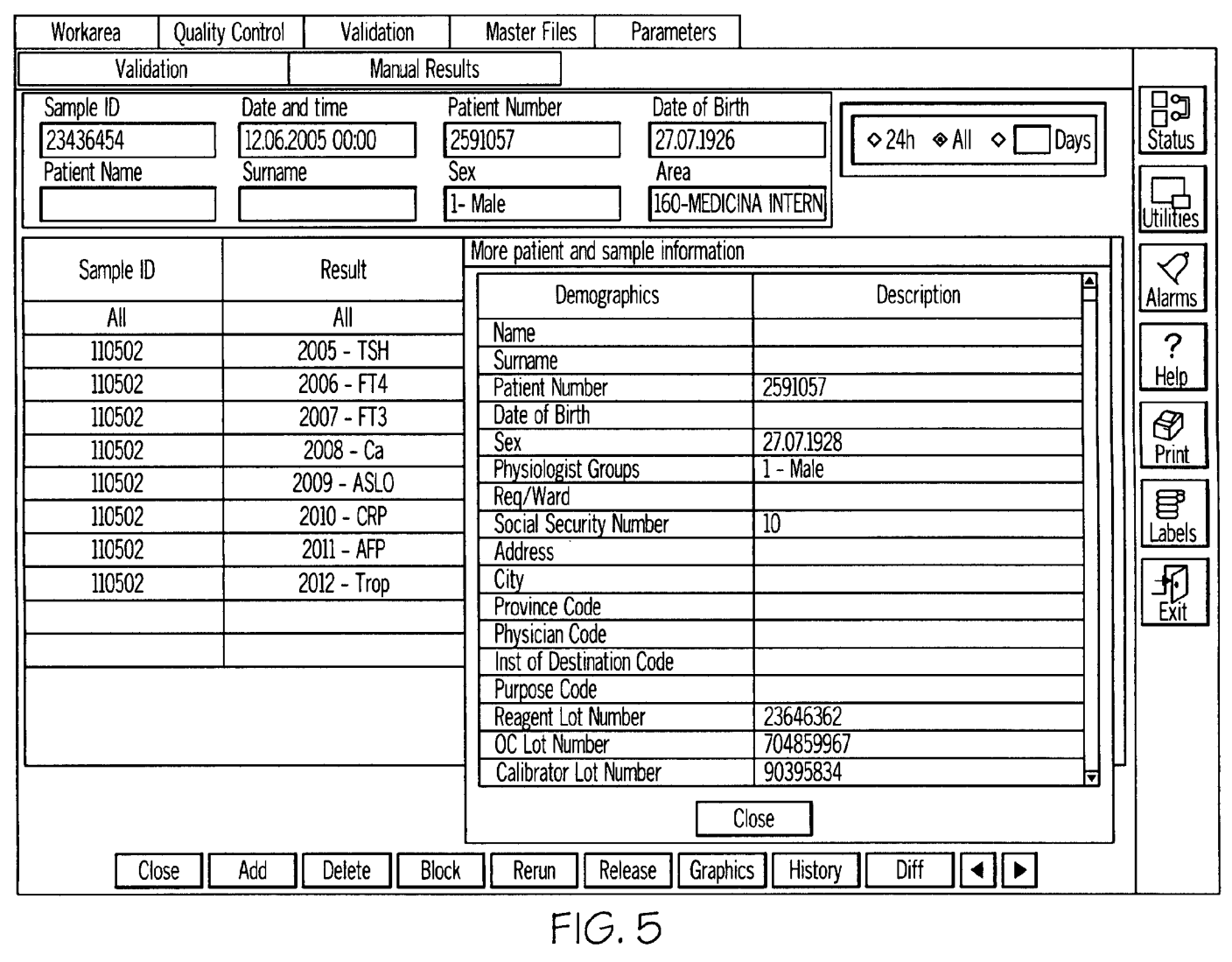

The test result context information is displayed in a first realization step in the PSM management unit as follows:
Integra 400/800 systems is uploading the reagent, control and calibrator lot-number information via the standard host interface. PSM is storing this information in an appropriate database and linking them to the appropriate patient sample test results. The information can be accessed by a user and displayed as shown in FIG. 5.

In one embodiment a system for managing sample test results and respective sample result context information within a laboratory environment is disclosed. The system comprising at least one analytical unit 20 configured to run at least one test on a sample, a management unit 10 connected with the at least one analytical unit 20 for data interchange, wherein said management unit 10 is configured to save and display on demand sample test results and respective sample result context information, to control dynamically at least one actual value of at least one item of the respective sample result context information with respect to a scheduled threshold value and to initiate at least one action as soon as the actual value corresponds to the scheduled threshold value according to a predefined execution plan schedule.

In one embodiment of the system, the system further comprises at least one post-analytical unit configured to archive measured samples and/or at least one pre-analytical unit configured to prepare the sample for the analytical unit 20.

It is possible, in one embodiment, that the post-analytical unit and/or the pre-analytical unit can also be connected to the management unit 10 for data interchange.

Furthermore, in another embodiment, it is possible in case that at least one post—as well as at least one pre-analytical unit are provided, that those units are consolidated within one or more common physical equipment.

According to a further possible embodiment of the system, the management unit 10 can communicate with one or more host components via any standard host interface protocol, such as via ASTM or HL7.

According to a further embodiment of the system, the management unit 10 comprises a graphical user interface which provides an access to the sample test results and the respective sample result context information stored within a database of the management unit 10, thus allowing a user to retrieve the sample test results and the respective sample result context information of one or more samples belonging to a patient. The graphical user interface uses windows, icons and menus and can be manipulated by a user, e.g. via a computer-mouse or a keyboard, so that the user can effectively interact with the management unit by holding a kind of dialog. A window is a usually rectangular portion of an appropriate display screen that can display its contents, e.g. a program, icons, a text file or an image seemingly independent of the rest of the display screen. Icons can be provided which generally represent a specific program, a file, a directory or a device. Therefore, commands can be issued in the graphical user interface by using for example a computer-mouse, a trackball or a touchpad to first move a pointer on the display screen to, or on top of, the icon, menu item or window of interest in order to select that object. Then, for example, icons and windows can be moved by dragging and objects or programs can be opened by clicking on their icons.

The database can be an integral part of the management unit. Alternatively, the database can be separated from the management unit, but in direct contact therewith. A user can ask via the graphical user interface for displaying a certain sample test result and the respective sample result context information. This information can be displayed directly in a specific window of a display screen of the graphical user interface. But it is also possible that this information is displayed on a separate display screen, e.g. an appropriate result context screen.

The sample result context information can comprise at least the following items: a reagent lot number of a reagent package used for the sample test, a quality control (QC) lot number of a quality control material used for a quality control measurement made in connection with the sample test and a calibrator lot number of a calibrator material used for calibration purposes in connection with the sample test.

According to a further possible embodiment of the system, the sample test results and the respective sample result context information can be transferred at least partly automatically from the analytical unit 20 into the management unit 10.

Thereby, it is possible that the sample text results and the respective sample result context information can be uploaded from the analytical unit 20 to the management unit 10 via a standard host interface.

Alternatively, it is possible that the sample test results and the respective sample result context information can be uploaded periodically as a log-file from the analytical unit 20 to the management unit 10, such as via a high-speed network connection. The management unit 10 can filter the appropriate information out of the log-file for a consolidated data view. The log-file may comprise among other things lot number information of the used reagent material, quality-control material, calibrator material, number of determinations per reagent pack, expiration time, production date, etc.

Alternatively, it is also possible that a part of the sample result context information is incorporated within a two-dimensional barcode. The barcode information can also be scanned into the management unit 10, exemplarily in the database of the management unit. This information is linked with a corresponding sample test result after the sample test has been performed and the result has been uploaded by the analytical unit 20 to the management unit 10.

According to a further embodiment of the system, the at least one action initiated by the management unit 10 as soon as the fulfilment level (or actual value) corresponds to the scheduled fulfilment level (or threshold value) according to a predefined execution plan schedule is a signal informing the user that the predefined fulfilment level (or threshold value) is reached. Such a signal can be an acoustic signal or it can be an optical signal displayed on an appropriate screen connected with the management unit 10. In reaction of such a signal the user can react accordingly, e.g. by activating an order.

Such a signal can be given in case that one of the materials needed to perform a certain sample test isn't still available in a sufficiently high quantity. Therefore, it is possible to predefine a target value, e.g. a minimum amount for each of the different needed materials, corresponding to the scheduled predefined threshold value and as soon as the number of one of the needed materials corresponds or even undergoes the predefined target value the signal is given so that the missing material can be refilled/ordered, either manually or automatically.

Alternatively, it is possible to define the threshold value as a specific number of tests performed by the analytical unit 20. After having reached this number, the management unit 10 can trigger for example a routine maintenance of the analytical unit 20 followed by a reset of the number of performed tests.

It is also possible that the threshold value corresponds to a specific time period. When this time period is over, which can be easily derived from at least one item of the respective sample result context information the management unit 10 can trigger for example an evaluation of the performance of the analytical unit 20. A lot of further scenarios are imaginable in which a dynamic control and an initiation of an appropriate action can be useful. It is possible that a signal is generated in case the expiration time in any used item exceeds. The signal can be an acoustic signal or an optical signal.

In another embodiment, a method for managing sample test results and respective sample result context information within a laboratory environment is provided. The method comprising running at least one test on at least one sample by means of at least one analytical unit 20, and transferring the corresponding sample test results and the respective sample result context information from the at least one analytical unit 20 to a management unit 10 connected with the at least one analytical unit 20 for data interchange. The method further includes storing the sample test results and the respective sample result context information, displaying on demand the sample test results and the respective sample result context information, controlling dynamically at least one actual value of at least one item of the respective sample result context information with respect to a scheduled threshold value, and initiating at least one action in case that the actual value corresponds to the scheduled threshold value according to a predefined execution plan schedule.

In a possible embodiment of the method, the sample test results and the respective sample result context information is displayed on demand via a graphical user interface.

Furthermore, it is possible according to another embodiment of the method that the sample test results and the respective sample result context information is transferred at least partly automatically from the analytical unit 20 into the management unit 10. Sample test results and the respective sample result context information can be uploaded from the analytical unit 20 to the management unit 10 via a standard host interface.

It is possible that the uploaded result context information which is uploaded by the analytical unit 20 to the management unit 10 together with the sample test results includes at least the following items:

A reagent lot number of a reagent package which is used for the sample test measurement is uploaded from the analytical unit 20 to the management unit 10 with each patient sample test result.

A quality control lot number of a quality control material which is used for a quality control measurement to check if the analytical unit 20 is under control, is also uploaded by the analytical unit 20 to the management unit 10. Besides the quality control lot number also the reagent lot number used for a quality control measurement is uploaded from the analytical unit 20 to the management unit 10 when the quality control result is uploaded.

A calibrator lot number of a calibrator material which is used for calibration purposes is uploaded to the management unit 10. A calibrator lot number is uploaded as soon as the calibration process has been finished. Besides the calibrator lot number also the reagent lot number is uploaded.

Optionally, it is also possible, that not only the calibrator lot number but also a corresponding calibrator result is uploaded from the analytical unit 20 to the management unit 10.

Alternatively, it is possible that the analytical unit 20 is uploading a log-file periodically to the management unit 10. Part of the log-file information is the required respective sample result context information such as a quality control lot number for each control level, a calibrator lot number, optionally with a calibrator result, the reagent lot number used for the patient result measurement, expiration time, and number of determinations, i.e. bottle size. Due to the size the log-file will be transferred via a high-speed network connection to the management unit 10. The management unit 10 is filtering the appropriate information out of the log-file for a consolidated data view.

According to a further embodiment of the method, a label with a two-dimensional barcode is available on each reagent package, each quality control package and each calibrator package. Those two-dimensional barcodes have besides other information the required reagent lot information, quality control lot information and calibrator lot information. The barcode information is scanned into the database of the management unit 10. With each patient test result received from the analytical unit 20 the appropriate reagent information, quality control information and calibrator information is linked.

It is possible that another embodiment of the system may further comprises an appropriate result context screen which is intended to show on demand all sample test results and the respective sample result context information of one or more samples belonging to a patient.

To retrieve for example samples of a specific patient and to display the corresponding sample information including the sample test results and the respective sample result context information, a dialog via the graphical user interface is started to filter in the database of the system for the appropriate patient and the assigned sample(s). It is possible that a lot of different search criteria are supported.

It is possible for example to use the following search criteria to find the requested patient including the corresponding sample information in the database: Patient-ID (patient identity); Sample-ID; Patient name; Patient date of birth; Sample order date/time; and Date/time selection.

Those search criteria are very useful to find all information about a patient and assigned sample test results and respective sample result context information. Those search criteria can be feed into the management unit 10 via respective assigned entry fields of the dialog. The dialog is supported by appropriate windows, icons and menus, each of which are linked with indicated functionalities. It is possible to support in the patient-name, the patient-ID and the sample-ID entry field so-called wildcards. A wildcard character can be used to represent one or many characters as means of specifying more than one name or label during the search procedure. A wildcard character can be described as a special symbol that stands for one or more characters. Within the search procedure wildcards can be used for identifying patient and sample records. This enables a user to select multiple patient or sample records by a single specification.

By means of the above mentioned search criteria and the appropriate input parameters a query is started. As a result of such a query all samples are listed fulfilling the above mentioned search criteria. Those samples can be listed in an appropriate window on a specified above mentioned result context screen. It is possible that besides the listing of the samples further icons are provided on the screen allowing a user to display further background information. It is possible for example that a details button is provided which initiates when being pressed to display further sample information of a specific selected line of a first listed sample.

Generally, it is possible that a very detailed and specific dialog is opened which can be conducted via the above mentioned result context screen. During such a dialog, the selected patient sample including the sample test results and the respective sample result context information can be listed. The listing can be organized in form of a table with a number of columns. Each of those columns can be assigned, respectively, to one specific item of the patient sample information including the patient sample result context information. Those information items include for example a specification of a test requested for the patient sample, a result of the requested test, a measurement date and time of the requested test, a name of a specific validator(s) having done a technical validation of the test result, a name, e.g. a log-in name of the validator(s) having done a medical/clinical validation of the corresponding test result, a reagent lot number active at the time of the respective patient result measurement on a corresponding analytical unit 20, a reagent lot expiration time of the corresponding reagent lot active at the time of the corresponding patient result measurement on the analytical unit 20, and the analytical unit itself by means of which the corresponding sample test has been performed.

In addition to the information concerning the sample test itself, there are provided further columns or lines within the corresponding table representing all information about the quality control. The quality control information comprises for example a control code, a control result, a control measurement date and time, a control validator, a control lot number, a control expiration time, a control target value, control validation violation flags, a control command. Further items which are included by the sample result context information are a calibrator name, a calibrator result or status, a calibrator lot number, a calibrator curve and a calibrator expiration time.

The columns within the above mentioned table which are displayed on the appropriate result context screen and the column sequence on the different selected levels which can be shown are configurable.

The graphical user interface in another embodiment might provide further widgets such as buttons, menus, check boxes, scroll bars and rulers which are assigned to certain functionalities, respectively.

The present disclosure in one embodiment provides one source to store required information for a required time period enforced by statutory provisions. Furthermore, the present disclosure makes it possible to provide one front end to display a patient sample result and respective patient sample result context information. By means of the present disclosure it is easy to link required information coming from different sources. The information concerning a patient sample test result and respective sample result context information can be consolidated and delivered via an easy and convenient access. The error rate due to computer aided automated and semi-automated processes is decreased and therefore, the quality is increased. The present disclosure requires less administrative effort due to automated/semi-automated processes.

The present disclosure further covers in another embodiment a computer program product with a computer-readable medium and a computer program stored on the computer-readable medium with a program code which is suitable for carrying out a method according to any one of the embodiments provided by the present disclosure when the computer program is run on a computer, exemplarily on a computer which is incorporated within a system according to any one of the embodiment provided by the present disclosure.

The present disclosure in another embodiment also refers to a computer program with a program code, which is suitable for carrying out a method according to any one of the embodiment provided by the disclosure, when the computer program is run on a computer, exemplarily on a computer which is incorporated within a system according to any one of the embodiment provided by the present disclosure.

The disclosure also relates in one more embodiment to a computer-readable medium with a computer program stored thereon, the computer program comprising a program code, which is suitable for carrying out a method according to any one of the embodiments provided by the disclosure when the computer program is run on a computer, exemplarily on a computer integrated within a system and/or a management unit according to any one of the embodiment provided by the present disclosure.

What is claimed is:

1. A system for managing sample test results and respective sample result context information within a laboratory environment, the system comprising:
   at least one analytical unit configured to run at least one test on a sample,
   a management unit connected with the at least one analytical unit for data interchange, wherein said management unit is configured to save and display on demand sample test results and respective sample result context information, to control dynamically at least one actual value of at least one item of the respective sample result context information with respect to a scheduled threshold value and to initiate at least one action as soon as the actual value corresponds to the scheduled threshold value according to a predefined execution plan schedule, wherein the sample result context information comprises at least the following items: a reagent lot number of a reagent package used for the sample test, a QC lot number of a QC material used for a quality control measurement, and a calibrator lot number of a calibrator material used for calibration purposes.

2. The system according to claim 1, the system further comprising at least one post-analytical unit configured to archive measured samples and/or at least one pre-analytical unit configured to prepare the sample for the analytical unit.

3. The system according to claim 2, wherein the post-analytical unit and/or the pre-analytical unit can be connected to the management unit for data interchange.

4. The system according to claim 2, wherein the at least one post- and the at least one pre-analytical units are consolidated within one or more common physical equipment.

5. The system according to claim 1, wherein the management unit can communicate with a host component via any standard host interface protocol.

6. The system according to claim 5, wherein the management unit comprises a graphical user interface which provides an access to the sample test results and respective sample result context information stored within a database of the management unit, thus allowing a user to retrieve the sample test results and the respective sample result context information of one or more samples belonging to a patient.

7. The system according to claim 6, further comprising a result context screen which is intended to show on demand all sample test results and the respective sample result context information of one or more samples belonging to a patient.

8. The system according to claim 1, wherein the sample test results and respective sample result context information can be transferred at least partly automatically from the analytical unit into the management unit.

9. The system according to claim 8, wherein the sample test results and respective sample result context information can be at least partially uploaded from the analytical unit to the management unit via a standard host interface.

10. The system according to claim 8, wherein the sample test results and respective sample result context information can be at least partially uploaded periodically as a log-file from the analytical unit to the management unit.

11. The system according to claim 10, wherein the management unit can filter appropriate information out of the log-file for a consolidated data view.

12. The system according to claim 8, wherein a part of the sample result context information is incorporated via scan of a 2-dimensional barcode, available on the reagent package, the QC package, the calibrator package, and linked by the management unit with corresponding sample test results.

13. The system according to claim 1, wherein the at least one action initiated by the management unit is a signal informing a user that the predefined fulfilment level is reached.

14. A management unit for managing sample test results and respective sample result context information within a laboratory environment, the management unit comprising a database to save the sample test results and respective sample result context information, output means able to display on demand the sample test results and respective sample result context information, connecting means able to receive the sample test results and respective sample result context information from at least one analytical unit and means able to control dynamically at least one actual value of at least one item of the respective sample result context information with respect to a scheduled threshold value and to initiate at least one action as soon as the actual value corresponds to the scheduled threshold value according to a predefined execution plan schedule, wherein the sample result context information comprises at least the following items: a reagent lot number of a reagent package used for the sample test, a QC lot number of a QC material used for a quality control measurement, and a calibrator lot number of a calibrator material used for calibration purposes.

15. The management unit according to claim 14, wherein the output means comprise a graphical user interface.

16. The management unit according to claim 14, wherein the management unit can communicate with a host component via any standard host interface protocol.

17. A method for managing sample test results and respective sample result context information within a laboratory environment, the method comprising:
running at least one test on at least one sample by means of at least one analytical unit;
transferring the corresponding sample test results and the respective sample result context information from the at least one analytical unit to a management unit connected with the at least one analytical unit for data interchange;
storing the sample test results and the respective sample result context information;
displaying on demand the sample test results and the respective sample result context information;
controlling dynamically at least one actual value of at least one item of the respective sample result context information with respect to a scheduled threshold value; and
initiating at least one action in case that the actual value corresponds to the scheduled threshold value according to a predefined execution plan schedule,
wherein the sample result context information comprises at least the following items: a reagent lot number of a reagent package used for the sample test, a QC lot number of a QC material used for a quality control measurement, and a calibrator lot number of a calibrator material used for calibration purposes.

18. The method according to claim 17, wherein the sample test results and the respective sample result context information are displayed on demand via a graphical user interface.

19. The method according to claim 17, wherein the sample result context information further comprises at least the following items a QC lot number of a QC material for all quality control levels valid at the time of sample test measurement on the analytical unit, a calibrator lot number of a calibrator material valid at the time of sample test measurement on the analytical unit, calibrator status and calibrator curve valid at the time of sample test measurement on the analytical unit.

20. The method according to claim 17, wherein the sample test results and respective sample result context information is transferred at least partly automatically from the analytical unit into the management unit.

21. The method according to claim 17, wherein the sample test results and respective sample result context information is uploaded from the analytical unit to the management unit via a standard host interface.

22. The method according to claim 20, wherein the sample test results and respective sample result context information is uploaded periodically as a log-file from the analytical unit to the management unit.

23. The method according to claim 22, wherein the management unit is filtering appropriate information out of the log-file for a consolidated data view.

24. The method according to claim 20, wherein a part of the sample result context information is incorporated via scan of a 2-dimensional barcode which is linked by the management unit with corresponding sample test results.

25. The method according to claim 17, wherein the at least one action initiated by the management unit is chosen as a signal informing a user that the predefined fulfilment level is reached.

26. A non-transitory computer-readable medium having stored thereon a computer program which, when executed by a computer system, causes the computer system to perform a method for managing sample test results and respective sample result context information within a laboratory environment, the method comprising:
running at least one test on at least one sample by means of at least one analytical unit;
transferring the corresponding sample test results and the respective sample result context information from the at least one analytical unit to a management unit connected with the at least one analytical unit for data interchange;
storing the sample test results and the respective sample result context information;
displaying on demand the sample test results and the respective sample result context information;
controlling dynamically at least one actual value of at least one item of the respective sample result context information with respect to a scheduled threshold value; and
initiating at least one action in case that the actual value corresponds to the scheduled threshold value according to a predefined execution plan schedule,
wherein the sample result context information comprises at least the following items: a reagent lot number of a reagent package used for the sample test, a QC lot number of a QC material used for a quality control measurement, and a calibrator lot number of a calibrator material used for calibration purposes.

27. A computer program product comprising a non-transitory computer-readable medium according to claim 26.

28. A system for managing sample test results and respective sample result context information within a laboratory environment, the system comprising:
at least one analytical unit configured to run at least one test on a sample, a management unit connected with the at least one analytical unit for data interchange, wherein said management unit is configured to save and display on demand sample test results and respective sample result context information, to control dynamically at least one actual value of at least one item of the respective sample result context information with respect to a scheduled threshold value and to initiate at least one action as soon as the actual value corresponds to the scheduled threshold value according to a predefined execution plan schedule, wherein the sample result context information comprises at least the following items: a reagent lot number of a reagent package used for the sample test, a QC lot number of a QC material used for a quality control measurement, a calibrator lot number of a calibrator material used for calibration purposes, wherein the sample test results and respective sample result context information can be transferred at least partly automatically from the analytical unit into the management unit, wherein a part of the sample result context information is incorporated via scan of a 2-dimensional barcode, available on the reagent package, the QC package, the calibrator package, and linked by the management unit with corresponding sample test results.

29. A method for managing sample test results and respective sample result context information within a laboratory environment, the method comprising:
running at least one test on at least one sample by means of at least one analytical unit;
transferring the corresponding sample test results and the respective sample result context information from the at least one analytical unit to a management unit connected with the at least one analytical unit for data interchange;
storing the sample test results and the respective sample result context information;
displaying on demand the sample test results and the respective sample result context information;
controlling dynamically at least one actual value of at least one item of the respective sample result context information with respect to a scheduled threshold value; and
initiating at least one action in case that the actual value corresponds to the scheduled threshold value according to a predefined execution plan schedule, wherein the sample test results and respective sample result context information is transferred at least partly automatically from the analytical unit into the management unit, wherein a part of the sample result context information is incorporated via scan of a 2-dimensional barcode which is linked by the management unit with corresponding sample test results.

30. The system according to claim 1, wherein the at least one action comprises an output of a signal to a user indicating to the user that an actual stock of a reagent material has reached a minimum level.

31. The system according to claim 1, wherein the at least one action comprises triggering as soon as an actual stock of a reagent material undergoes a predefined value re-ordering of the reagent material.

32. The system according to claim 1, wherein the at least one action comprises an evaluation in order to optimize process sequences.

33. The management unit according to claim 14, wherein the at least one action comprises an output of a signal to a user indicating to the user that an actual stock of a reagent material has reached a minimum level.

34. The management unit according to claim 14, wherein the at least one action comprises triggering as soon as an actual stock of a reagent material undergoes a predefined value re-ordering of the reagent material.

35. The management unit according to claim 14, wherein the at least one action comprises an evaluation in order to optimize process sequences.

36. The method according to claim 17, wherein the at least one action comprises an output of a signal to a user indicating to the user that an actual stock of a reagent material has reached a minimum level.

37. The method according to claim 17, wherein the at least one action comprises triggering as soon as an actual stock of a reagent material undergoes a predefined value re-ordering of the reagent material.

38. The method according to claim 17, wherein the at least one action comprises an evaluation in order to optimize process sequences.

39. The non-transitory computer-readable medium according to claim 26, wherein the at least one action comprises an output of a signal to a user indicating to the user that an actual stock of a reagent material has reached a minimum level.

40. The non-transitory computer-readable medium according to claim 26, wherein the at least one action comprises triggering as soon as an actual stock of a reagent material undergoes a predefined value re-ordering of the reagent material.

41. The non-transitory computer-readable medium according to claim 26, wherein the at least one action comprises an evaluation in order to optimize process sequences.

* * * * *